US000001935H

(19) United States

(12) Statutory Invention Registration (10) Reg. No.: US H1935 H

Wilhoit et al. (43) Published: Jan. 2, 2001

(54) COMBINATION POUCH AND RELEASE SHEET AND METHOD FOR PRODUCING SAME

(75) Inventors: Darrel Loel Wilhoit, Plainfield, IL (US); James D. Tribble, Brazil, IN (US)

(73) Assignee: Tredegar Corporation, Richmond, VA (US)

(21) Appl. No.: 08/938,340

(22) Filed: Sep. 26, 1997

(51) Int. Cl.[7] ..... B32B 1/00; B32B 9/00; B32B 7/12; B32B 9/04

(52) U.S. Cl. ..... 428/174; 428/41.8; 428/352; 428/447

(58) Field of Search ..... 428/41.8, 447, 428/174, 187, 352, 473, 472; 264/483, 173.19, 173.16, 211.12, 280, 282, 286; 604/387, 390; 156/244.23, 244.24, 244.17, 272.6

(56) References Cited

U.S. PATENT DOCUMENTS

| | | | |
|---|---|---|---|
| 3,399,156 | 8/1968 | Bell | 260/29.1 |
| 3,632,386 | 1/1972 | Hurst | 117/46 |
| 3,936,582 | 2/1976 | Keiser | 428/447 |
| 4,348,457 | 9/1982 | Rosenthal et al. | 428/349 |
| 4,419,410 | 12/1983 | Weiner | 428/516 |
| 4,419,411 | 12/1983 | Park | 428/516 |
| 4,425,176 | 1/1984 | Shibano et al. | 156/244.11 |
| 4,535,020 | 8/1985 | Thomas et al. | 428/131 |
| 4,569,712 | 2/1986 | Shibano et al. | 156/244.14 |
| 4,647,524 | 3/1987 | Sullivan | 430/312 |
| 4,678,465 | 7/1987 | Avejic | 604/397 |
| 4,902,378 | 2/1990 | Ouderkirk et al. | 156/643 |
| 4,968,578 | 11/1990 | Light et al. | 430/126 |
| 4,978,436 | 12/1990 | Kelly | 204/165 |
| 5,169,900 | 12/1992 | Gudelis | 525/106 |
| 5,188,395 | 2/1993 | Kawahara et al. | 283/113 |
| 5,302,427 | 4/1994 | Murschall et al. | 428/34.2 |
| 5,324,779 | 6/1994 | Jarrin et al. | 525/57 |
| 5,370,930 | 12/1994 | Ito | 428/335 |
| 5,413,568 | 5/1995 | Roach et al. | 604/358 |
| 5,422,175 | 6/1995 | Ito et al. | 428/304.4 |
| 5,436,073 | 7/1995 | Williams et al. | 428/343 |
| 5,462,166 | 10/1995 | Minton et al. | 206/440 |
| 5,468,714 | 11/1995 | Oshima et al. | 503/227 |
| 5,470,900 | 11/1995 | Sasaki et al. | 524/269 |
| 5,484,636 | 1/1996 | Berg, Jr. et al. | 428/40 |
| 5,489,473 | 2/1996 | Wilkie | 428/323 |
| 5,496,072 | 3/1996 | Yamauchi et al. | 283/86 |
| 5,516,563 | 5/1996 | Schumann et al. | 428/34.2 |
| 5,563,190 | 10/1996 | Fujimura | 524/15 |
| 5,569,228 | 10/1996 | Byrd et al. | 604/385.1 |
| 5,569,230 | 10/1996 | Fisher et al. | 604/385.1 |
| 5,571,569 | 11/1996 | Kato et al. | 427/493 |
| 5,576,818 | 11/1996 | Badesha et al. | 355/271 |
| 5,618,618 | 4/1997 | Murschall et al. | 428/331 |
| 5,972,473 * | 10/1999 | Arakawa et al. | 428/141 |

FOREIGN PATENT DOCUMENTS

| | | |
|---|---|---|
| 53-58578 | 5/1978 | (JP) . |
| 61-200879 | 9/1986 | (JP) . |

OTHER PUBLICATIONS

XP–002106474, Aug. 13, 1991, One page abstract "Double–sided adhesive tape produce . . . ".

XP–002106475, Mar. 10, 1986, One page abstract "Adhesive Sheet Comprise Base Sheet Adhesive Agent . . . ".

XP–002106476, Oct. 13, 1986, One page abstract "Release Paper Produce Adhesive Tape Label Electric Charge Silicone . . . ".

Statutory Registration H1454 (1995).

* cited by examiner

*Primary Examiner*—Charles T. Jordan

*Assistant Examiner*—Aileen J. Baker

(74) *Attorney, Agent, or Firm*—Jenkens & Gilchrist, P.C.

(57) ABSTRACT

An improved release sheet for use in connection with a sanitary catamenial pad is disclosed. The improved release sheet exhibits superior noise, drape, bulk and gloss characteristics due to its method of production. A polyethylenic release material containing silicone capable of being fixed within the surface of the release material is coextruded with at least a base film to provide a film which is also embossed to provide a combination pouch and release sheet with superior physical characteristics. Corona treatment of the release material layer preferably occurs following embossing, but can occur prior to embossing or both prior to and following embossing to fix the silicone within the surface of the release material. In-line recycling of materials provides additional cost advantages.

35 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

COMBINATION POUCH AND RELEASE SHEET AND METHOD FOR PRODUCING SAME

BACKGROUND OF THE INVENTION

Polyolefins and particularly polyethylenes are good base materials for films, coatings and release films. Such materials are easily formulated into films which exhibit desired slip, release, peelability and related characteristics. These films are known in the form of release films applied to adhesive materials, such as removable protective layers for adhesive strips and the like. The protective layer prevents premature adhesion from the strip and protects the covered area from dust, contamination, etc.

Polymer blends containing silicone are advantageous in the production of release films. However, films containing silicone have traditionally suffered from movement of the silicone within the film layers or across layers, also known as "migration". For example, polyolefinic films containing silicone suffer from the tendency for the silicone to migrate from the surface of the film. Since it is the presence of silicone at the surface of the film which imparts desired physical characteristics (e.g., slip, release) to the film, any movement of the silicone away from the surface diminishes, if not completely removes, such advantageous characteristics.

Although the use of high dose corona treatment is known to inhibit migration of silicone within the surface of a film, the prior art does not disclose, teach or suggest the use of corona treatment in combination with embossing to substantially enhance the performance characteristics of silicone-containing polymeric films.

It has been discovered that the use of embossing techniques in combination with corona treatment of a silicone-containing polymeric film substantially improves the performance characteristics of such film as a release sheet. Such improved characteristics include lower peel forces, lower noise generated during the peel process, improved drape and tactile properties and increased bulk.

Traditional approaches to release films designed for use in connection with personal hygiene products include coated films and papers, which involves coating a paper with silicone and adhering it to a film. However, such traditional release films suffer from relatively high peel forces and inferior noise, drape and bulk characteristics. Moreover, such traditional, inferior performing films are relatively expensive.

Thus there remains a need for an economical polyethylenic-based film for use as a combination pouch and release sheet in connection with personal hygiene products, such as sanitary catamenial pads, which is capable of being extruded or coextruded with silicone and exhibits improved performance and aesthetic characteristics, and a method for producing same.

SUMMARY OF THE INVENTION

In accordance with the present invention there is provided an improved combination pouch and release sheet composed of a silicone-containing embossed polyolefinic material. The film is corona treated to prevent migration of the silicone material within the film. Since the invention avoids the traditional need for a separate release paper and is produced using an in-line process, the combination pouch and release sheet of the present invention exhibits superior performance while being less expensive than such traditional release sheets.

The improved combination pouch and release film of the present invention comprises a single- or multiple-layer film. Preferably, a polyolefinic material containing a silicone component is used as a release material. The release material is extruded or coextruded with at least a polyolefinic film not containing silicone using traditional methods. Following extrusion (or coextrusion), the film is embossed to impart superior physical and aesthetic characteristics to the film. The release layer is then corona treated to prevent migration of the silicone in release layer. Corona treating the film either prior to or following embossing is contemplated by the combination pouch and release sheet of the present invention. Preferably, the film is embossed first and then corona treated; however, as previously mentioned, the film can be corona treated at any point, and even at multiple points, of the process. Embossing is accomplished via traditional embossing methods.

The resulting film exhibits superior drape, texture, gloss, noise and peel force characteristics. Moreover, unlike many release films, the superior release properties of the release film of the present invention are not diminished over time in contact with a pressure sensitive adhesive.

According to a method of the present invention, the improved combination pouch and release film of the present invention is produced by extruding a thin layer of a polyolefinic release material containing a silicone component. In one embodiment, the polyolefinic material containing silicone is coextruded onto a base film (preferably of non-silicone-containing polyolefin) to form a film and subsequently treated with a corona discharge. Corona treatment prevents the silicone material from migrating within the film. Either before or after corona treatment, but preferably before, the film is embossed to enhance the release, tactile and aesthetic characteristics of the resultant film. Again, the corona treatment step can even occur at multiple steps within the process either before and/or after embossing.

In another embodiment of the method of the present invention, a release material containing silicone and a base material not containing silicone are coextruded with a base film (also not containing silicone) to form an upper layer (release material), a core layer (base film) and a lower layer (base material). The multilayered film is then preferably embossed. Following embossing, the release material layer is subjected to corona treatment to fix the silicone within the release material. As discussed above, the release material layer can be corona treated to prevent migration of the silicone prior to embossing, and can even be corona treated both prior to and following embossing.

Due to the in-line corona treatment of the film, there is no need for the time and expense associated with the traditional steps of coating and curing the film. The present method features in-line recycling of the process remnants from the film into the core layer, thus providing yet additional cost savings. Remnants from the film of a two layer coextrusion are recycled into the base film.

BRIEF DESCRIPTION OF THE FIGURES

A more complete understanding of the present invention may be had by reference to the following detailed description when taken in conjunction with the accompanying figures wherein.

DETAILED DESCRIPTION OF FIGURES

A combination pouch and release sheet is provided which exhibits superior physical characteristics, such as low gloss and low noise and improved release, drape and bulk. These superior physical characteristics are due to the unique combination of corona treatment of a silicone-containing film together with embossing of the film before and/or after such corona treatment.

Figure 1:
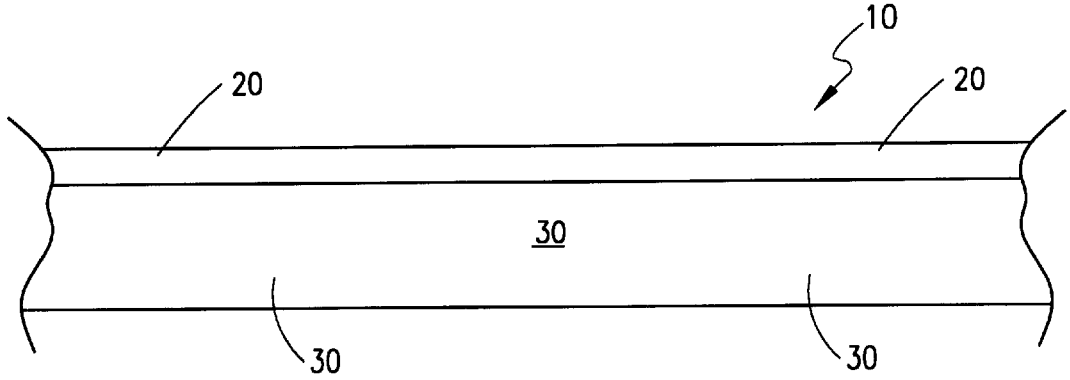
FIG. 1 (PRIOR ART)
FIG. 1 is an unembossed, corona treated silicone-containing flat release film.

In FIG. 1, there is shown a traditional unembossed release sheet 10, having a release layer 20 and a base layer 30. Since the traditional release sheet 10 is unembossed, it does not exhibit the superior physical and aesthetic characteristics of the improved combination pouch and release sheet of the present invention.

Figure 2:
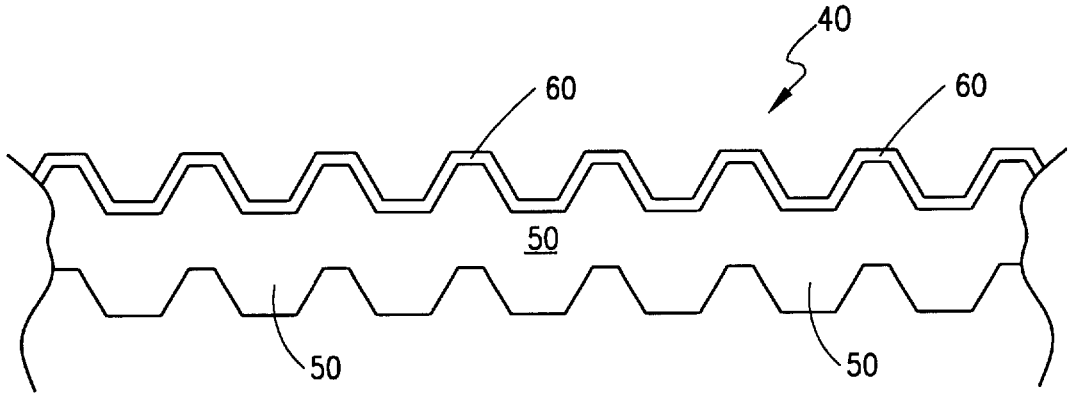
FIG. 2 illustrates a two-layer embodiment of the improved combination pouch and release sheet of the present invention.

In a preferred embodiment, illustrated in FIG. 2, the improved combination pouch and release sheet 40 of the present invention is of a two layer construction having a relatively thick (approximately 90% of the total thickness of the film) base film layer 50 and a relatively thin (the remaining approximately 10% of the total thickness) release layer 60. The relatively thick base film layer 50 is preferably constructed of a silicone-free polyolefin polymer, such as a ethylenic homopolmer or copolymer. Mixtures and blends of the foregoing materials may also be used, if desired. Such materials are preferred because they exhibit desired embossing characteristics. These materials are not intended as an exhaustive list of acceptable materials.

The silicone present in the relatively thin release layer 60 can be locked into place using corona treatment. An example of a preferred silicone-containing thin release layer 60 material for the improved combination pouch and release sheet 40 of the present invention is a silicone-containing polyethylene known as BYNEL 534, available from Dupont Canada.

Additionally, additives such as stabilizers, anti-block and slip agents may be added to the material comprising the base film layer 50. Fillers, such as titanium dioxide, mica, calcium, talc and the like, and pigments or dyes may also be added, as desired.

In the preferred embodiment, the improved combination pouch and release sheet 40 is composed of two or more layers coextruded using traditional methods known in the art. Coextrusion of the two or more layers cojoins the layers by forming a strong bond between the individual layers. Although a multilayered embodiment is preferred, it is noted that a monolayer embodiment extruded using techniques known in the art is also contemplated by the present invention.

The coextruded film is subjected to corona treatment to prevent the migration of the silicone material from the polyolefinic material of the thin release layer 60. Corona treatment chemically locks the silicone into the relatively thin release layer 60 through ionic attraction such that migration of the silicone is thereafter prevented. Since it is the presence of the silicone material in the surface of the relatively thin release layer 60 of the film which provides many of the superior physical properties of the improved release sheet, it is important the silicone material remain fixed in the surface and does not travel or otherwise migrate during or after production of the film. The stationary silicone material also provides the resultant release sheet with superior release properties unaffected by time in contact with a pressure sensitive adhesive. Corona treatment may be accomplished using techniques known in the art, such as by passing the film between a grounded cylindrical electrode and an overlying high potential electrode which form an arch over the grounded roll.

Embossing of the coextruded multilayered film can be carried out to affect varying degrees of embossing. Substantial performance and aesthetic improvements have been discovered both where the film is "shallow" embossed (e.g., 30% increased low load caliper) and where "deep" embossing (e.g., up to 100% increase in low load caliper) is accomplished. Various degrees and geometries of embossing can be employed within the scope of the present invention.

The resultant improved combination pouch and release sheet 40 exhibits up to 85% less peel force than traditional release sheets, 30–100% more bulk than nonembossed release sheets and superior noise and drape characteristics, both highly important in the personal hygiene product applications, such as pouches for sanitary napkins.

Figure 3:
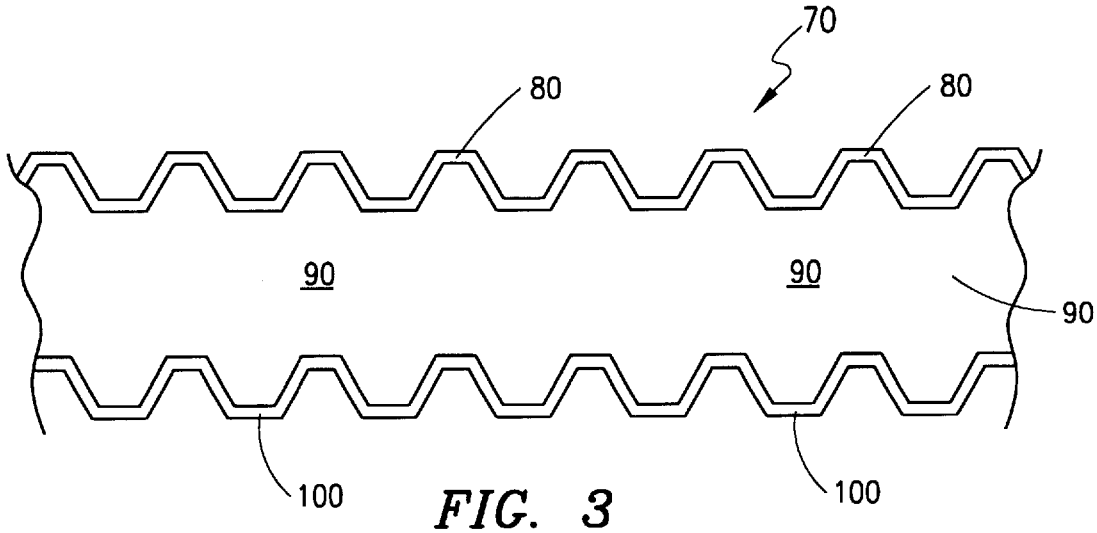
FIG. 3 illustrates a three-layer embodiment of the improved combination pouch and release sheet of the present invention.

As illustrated in FIG. 3, another embodiment of the improved combination pouch and release sheet 70 of the present invention comprises three layers. A relatively thin release material layer 80, a relatively thick base film 90 and a relatively thin base material layer 100 comprise this embodiment. The base film layer 90 is analogous to the base film layer 50 of the preferred embodiment described above and is constructed of a silicone-free polyolefin polymer, such as a ethylenic homopolmer or copolymer. Likewise, the thin release layer 80 is preferably constructed of a material containing silicone. The silicone present in the relatively thin release layer 80 can be locked into place using corona treatment. As with the preferred embodiment, the silicone-containing polyethylene known as BYNEL 534 is a preferred material for the thin release layer 80. The embossing technique, additives, extrusion/coextrusion techniques for the three layered embodiment are as described above for the preferred two-layer embodiment.

With the three-layered embodiment, in-line recycling of the process remnants into the core layer of the combination pouch and release sheet (rather than the base film) is accomplished. This feature provides added cost reduction to the resulting combination pouch and release sheet.

According to a method of the present invention the above-identified improved combination pouch and release sheet is produced by employing the steps of: preselecting a release material, preferably a polyethylenic material containing silicone which can be locked into place within the surface of the material; preselecting a base film for use with the release material, preferably a polyethylenic material not containing silicone; coextruding a thin layer of the release material containing silicone with a layer of the base film; and subjecting the top layer (release material) to corona treatment to prevent migration of the silicone material either before or after or both before and after embossing the resultant multilayered film to impart superior physical characteristics.

A different embodiment of the method of the present invention includes the following steps; preselecting a release material containing silicone; preselecting a base material not containing silicone; preselecting a base film not containing silicone; coextruding the base film between an upper layer of the release material and a lower layer of the base material such that the base film, or core layer, is sandwiched between the upper layer (release layer) and the lower layer (base material); subjecting the upper layer (release material) to corona treatment to prevent migration of the silicone material either before, after or both prior to and following embossing the resultant multilayered film to impart superior physical characteristics.

An ideal product category for use of the improved release sheet of the present invention is the personal hygiene industry, including sanitary catamenial pads and the like. The increased bulk, low noise, low gloss and superior drape make the improved release sheet ideal for use as a combination pouch and release sheet for such products.

One of the superior physical characteristics of the combination pouch and release sheet of the present invention, improved release values, is illustrated in the following table.

TABLE I

| 180 Degree Peel Test | | | |
|---|---|---|---|
| Sample No. | Max. Peel Strength grams/in. | Min. Peel Strength grams/in. | Avg. Peel Strength grams/in. |
| 3 | 25.1 | 21.8 | 23.6 |
| 5 | 25.2 | 21.2 | 23.7 |
| 11 | 15.4 | 12.8 | 13.7 |
| 13 | 18.8 | 18.2 | 18.5 |

In Table I above, film Samples Nos. 3 and 11 are the same film, prepared using the same production process, except that Sample 3 was left unembossed and Sample 11 was embossed. Likewise, film Samples Nos. 5 and 13 are identical films, prepared according to the same production process, except that Sample No. 5 was left unembossed and Sample No. 13 was embossed. The samples were then subject to peel strength testing at 180 degrees in accordance with Tribble Release Test Standard. The amount of force necessary to peel the samples was then measured and recorded in grams. Sixteen measurements for each film was recorded.

As demonstrated in Table I, Sample Nos. 11 and 13, the embossed film samples, demonstrated superior peel strength numbers in that less force was required to peel the embossed film samples, Sample Nos. 11 and 13, than was required with the unembossed samples, Sample Nos. 3 and 5.

It is important to note that release values noted above are for films prepared according to the present invention method, except for Sample Nos. 3 and 5, which were not embossed. Traditional films not prepared according to the method of the present invention exhibit peel strength values of approximately 60 grams/in., or approximately three-four times that exhibited by the improved combination pouch and release sheet of the present invention.

Although preferred embodiments of the invention have been described in the foregoing Detailed Description, it will be understood that the invention is not limited to the embodiments disclosed, but is capable of numerous rearrangements and modifications of parts and elements without departing from the spirit of the invention.

What is claimed is:

1. A sheet having improved release properties, said sheet comprising:

a release material containing silicone;

a base film;

said release material coextruded with said base film to form a multilayered release film; said release material corona treated to fix into position on a molecular level said silicone; and said release film including an embossed surface.

2. The sheet of claim 1, wherein the release material is a polyolefin.

3. The sheet of claim 1, wherein the release material is a polyethylemic polymer.

4. The sheet of claim 1, wherein the base film is a polyolefin.

5. The sheet of claim 1, wherein the base film does not contain silicone.

6. The sheet of claim 1, wherein the base film comprises a polyethylenic material.

7. The sheet of claim 1, wherein the multilayered release film is embossed.

8. The sheet of claim 7, wherein said release material is corona treated after the release film is embossed.

9. The sheet of claim 7, wherein said release material is corona treated before the release film is embossed.

10. The sheet of claim 7, wherein said release material is corona treated both prior to and following embossing of the release film.

11. The sheet of claim 1, wherein the sheet is used in connection with a combination pouch and release sheet for a sanitary catamenial pad.

12. The sheet of claim 1, wherein the base film is comprised of a polyolefin containing silicone.

13. A combination pouch and sheet having improved release properties, said combination pouch and sheet comprising:

an upper layer comprised of a polyethylenic polymer release material containing silicone;

a core layer comprised of a polyolefin base film not containing silicone;

a lower layer comprised of a polyolefin base material not containing silicone;

said core layer coextruded with said upper layer and said lower layer to form a multilayered release film;

said upper layer corona treated to fix into position on a molecular level said silicone; and said multilayered release film embossed to provide said sheet.

14. The combination pouch and sheet of claim 13, wherein the core layer is comprised of a polyolefin base film containing silicone.

15. A method for the production of a sheet having improved release properties, said sheet comprising the steps of:

preselecting a release material;

preselecting a base material;

preselecting a base film;

coextruding a layer of said release material and a layer of said base material on opposing sides of a layer of the base film to form a release film;

embossing the release film to provide improved physical characteristics; and corona treating the surface of the release material layer of the release film.

16. The method of claim 15, wherein the steps of preselecting a release material and a base material include the selection of polyolefins.

17. The method of claim 15, wherein the step of preselecting a release material includes the selection of a polyethylenic polymer containing silicone.

18. The method of claim 15, wherein the step of preselecting a base material includes the selection of a polyethylenic polymer not containing silicone.

19. The method of claim 15, wherein the step of preselecting a base film includes the selection of a polyolefin.

20. The method of claim 15, wherein the step of preselecting a base film includes selection of a polyethylenic polymer not containing silicone.

21. The method of claim 15, wherein the sheet is used as a combination pouch and release sheet for a sanitary catamenial pad.

22. The method of claim 15, wherein the release material layer is corona treated after the sheet is embossed.

23. The method of claim 15, wherein the release material layer is corona treated before the sheet is embossed.

24. The method of claim 15, wherein the release is corona treated both prior to and following embossing the sheet.

25. A method for the production of a sheet having improved release properties, comprising the steps of:

preselecting a release material of polyethylenic polymer containing silicone;

preselecting a base film of polyethylenic polymer not containing silicone;

coextruding at least one layer of said release material onto a layer of said base film to form a release film;

embossing said release film; and corona treating the surface of the release material layer of the release film to fix into position on a molecular level the silicone.

26. The method of claim 25, wherein the sheet is used as a combination pouch and release sheet for a sanitary catamenial pad.

27. The method of claim 25, wherein the release material layer is corona treated after the release film is embossed.

28. The method of claim 25, wherein the release material layer is corona treated before the release film is embossed.

29. The method of claim 25, wherein the release material is corona treated both prior to and following embossing of the release film.

30. The sheet of claim 1, wherein said release material layer is less than about 10% of the total thickness of said multilayered release film.

31. The combination pouch and sheet of claim 13, wherein said upper layer is less than about 10% of the total thickness of said multilayered release film.

32. The combination pouch and sheet of claim 31, wherein said lower layer is less than about 10% of the total thickness of said multilayered release film.

33. The method of claim 15, wherein the layer of said release material is less than about 10% of the total thickness of said release film.

34. The method of claim 33, wherein the layer of said base material is less than about 10% of the total thickness of said release film.

35. The method of claim 25, wherein the layer of said release material is less than about 10% of the total thickness of said release film.

* * * * *